(12) United States Patent  (10) Patent No.: US 8,634,917 B2
Conley et al.  (45) Date of Patent: *Jan. 21, 2014

(54) METHOD AND SYSTEM FOR IDENTIFYING AND DISPLAYING GROUPS OF CARDIAC ARRHYTHMIC EPISODES

(75) Inventors: Vickie L. Conley, Woodbury, MN (US); Allan T. Koshiol, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 790 days.

This patent is subject to a terminal disclaimer.

(21) Appl. No.: 12/220,830

(22) Filed: Jul. 29, 2008

(65) Prior Publication Data

US 2009/0036942 A1  Feb. 5, 2009

Related U.S. Application Data

(63) Continuation of application No. 11/021,141, filed on Dec. 22, 2004, now Pat. No. 7,418,295, which is a continuation of application No. 10/118,537, filed on Apr. 8, 2002, now Pat. No. 6,843,801, which is a continuation of application No. 09/378,406, filed on Aug. 20, 1999, now Pat. No. 6,418,340.

(51) Int. Cl.
*A61N 1/00* (2006.01)

(52) U.S. Cl.
USPC ............................................. 607/32; 600/523

(58) Field of Classification Search
USPC ............................... 600/508–523; 607/30–33
See application file for complete search history.

(56) References Cited

U.S. PATENT DOCUMENTS

| 4,006,737 A | 2/1977 | Cherry |
| 4,090,505 A | 5/1978 | Mortara |
| 4,166,470 A | 9/1979 | Neumann |
| 4,172,459 A | 10/1979 | Hepp |
| 4,187,854 A | 2/1980 | Hepp et al. |
| 4,316,249 A | 2/1982 | Gallant et al. |
| 4,336,810 A | 6/1982 | Anderson et al. |
| 4,509,530 A | 4/1985 | Curtis et al. |
| 4,529,401 A | 7/1985 | Leslie et al. |

(Continued)

FOREIGN PATENT DOCUMENTS

| EP | 0491649 | 6/1992 |
| EP | 0558353 | 9/1993 |
| EP | 0565084 | 10/1993 |
| EP | 0711531 | 5/1996 |

OTHER PUBLICATIONS

"U.S. Appl. No. 09/372,157, Amendment and Response mailed Jul. 25, 2001", 11 pgs.

(Continued)

*Primary Examiner* — Scott Getzow
(74) *Attorney, Agent, or Firm* — Schwegman Lundberg & Woessner, P.A.

(57) ABSTRACT

A medical device system that receives cardiac data representing a plurality of stored arrhythmic episodes, and analyzing the cardiac data to identify and display a subset of stored arrhythmic episodes as a function of user-specified episode criteria. The medical device system presents a query window on an interactive display in order to receive user-specified episode criteria via one or more input fields. The medical device displays only those episodes matching the episode criteria such as arrhythmia type, zone of detection, date of occurrence and average heart rate in beats per minute (BPM).

20 Claims, 6 Drawing Sheets

(56) References Cited

U.S. PATENT DOCUMENTS

| | | | |
|---|---|---|---|
| 4,549,552 A | 10/1985 | Groch et al. | |
| 4,680,708 A | 7/1987 | Ambos et al. | |
| 4,800,883 A | 1/1989 | Winstrom | |
| 4,809,697 A | 3/1989 | Causey, III et al. | |
| 4,825,869 A | 5/1989 | Sasmor et al. | |
| 4,850,357 A | 7/1989 | Bach, Jr. | |
| 4,947,857 A | 8/1990 | Albert et al. | |
| 4,964,410 A | 10/1990 | Leahey et al. | |
| 4,974,598 A | 12/1990 | John | |
| 4,989,610 A | 2/1991 | Patton et al. | |
| 4,998,531 A | 3/1991 | Bocchi et al. | |
| 5,000,189 A | 3/1991 | Throne et al. | |
| 5,012,814 A | 5/1991 | Mills et al. | |
| 5,027,824 A | 7/1991 | Dougherty et al. | |
| 5,046,504 A | 9/1991 | Albert et al. | |
| 5,047,930 A | 9/1991 | Martens et al. | |
| 5,050,612 A | 9/1991 | Matsumura | |
| 5,052,395 A | 10/1991 | Burton et al. | |
| 5,111,816 A | 5/1992 | Pless et al. | |
| 5,113,869 A | 5/1992 | Nappholz et al. | |
| 5,129,392 A | 7/1992 | Bardy et al. | |
| 5,193,550 A | 3/1993 | Duffin | |
| 5,215,083 A | 6/1993 | Drane et al. | |
| 5,217,021 A | 6/1993 | Steinhaus et al. | |
| 5,273,049 A | 12/1993 | Steinhaus et al. | |
| 5,279,293 A | 1/1994 | Andersen et al. | |
| 5,292,341 A | 3/1994 | Snell | |
| 5,299,118 A | 3/1994 | Martens et al. | |
| 5,309,919 A * | 5/1994 | Snell et al. | 600/510 |
| 5,311,873 A | 5/1994 | Savard et al. | |
| 5,311,874 A | 5/1994 | Baumann et al. | |
| 5,312,441 A | 5/1994 | Mader et al. | |
| 5,315,512 A | 5/1994 | Roth | |
| 5,341,811 A | 8/1994 | Cano | |
| 5,342,402 A | 8/1994 | Olson et al. | |
| 5,411,530 A | 5/1995 | Akhtar | |
| 5,421,830 A | 6/1995 | Epstein et al. | |
| 5,458,623 A | 10/1995 | Lu et al. | |
| 5,464,433 A | 11/1995 | White et al. | |
| 5,487,754 A * | 1/1996 | Snell et al. | 607/27 |
| 5,487,755 A | 1/1996 | Snell et al. | |
| 5,513,645 A | 5/1996 | Jacobson et al. | |
| 5,535,753 A | 7/1996 | Petrucelli et al. | |
| 5,549,654 A | 8/1996 | Powell | |
| 5,555,888 A | 9/1996 | Brewer et al. | |
| 5,578,063 A | 11/1996 | Bocek et al. | |
| 5,584,298 A | 12/1996 | Kabal | |
| 5,603,331 A | 2/1997 | Heemels et al. | |
| 5,607,460 A | 3/1997 | Kroll et al. | |
| 5,613,495 A | 3/1997 | Mills et al. | |
| 5,626,620 A | 5/1997 | Kieval et al. | |
| 5,626,623 A | 5/1997 | Kieval et al. | |
| 5,628,321 A | 5/1997 | Scheib et al. | |
| 5,643,255 A | 7/1997 | Organ | |
| 5,647,369 A | 7/1997 | Petrucelli et al. | |
| 5,674,249 A | 10/1997 | De Coriolis et al. | |
| 5,683,431 A | 11/1997 | Wang | |
| 5,697,959 A | 12/1997 | Poore | |
| 5,713,366 A | 2/1998 | Armstrong et al. | |
| 5,716,383 A | 2/1998 | Kieval et al. | |
| 5,716,384 A | 2/1998 | Snell | |
| 5,722,999 A | 3/1998 | Snell | |
| 5,724,985 A | 3/1998 | Snell et al. | |
| 5,743,268 A | 4/1998 | Kabal | |
| 5,749,906 A | 5/1998 | Kieval et al. | |
| 5,749,907 A | 5/1998 | Mann | |
| 5,772,604 A | 6/1998 | Langberg et al. | |
| 5,788,640 A | 8/1998 | Peters | |
| 5,792,203 A | 8/1998 | Schroeppel | |
| 5,792,204 A | 8/1998 | Snell | |
| 5,817,137 A | 10/1998 | Kaemmerer | |
| 5,833,623 A | 11/1998 | Mann et al. | |
| 5,891,179 A | 4/1999 | Er et al. | |
| 5,924,989 A | 7/1999 | Polz | |
| 5,951,484 A | 9/1999 | Hoium et al. | |
| 5,954,664 A | 9/1999 | Seegobin | |
| 5,961,467 A | 10/1999 | Shimazu et al. | |
| 5,974,341 A | 10/1999 | Er et al. | |
| 6,004,276 A | 12/1999 | Wright et al. | |
| 6,016,442 A * | 1/2000 | Hsu et al. | 600/518 |
| 6,017,307 A | 1/2000 | Raines | |
| 6,091,990 A | 7/2000 | Hsu et al. | |
| 6,253,102 B1 | 6/2001 | Hsu et al. | |
| 6,263,244 B1 | 7/2001 | Mann et al. | |
| 6,289,248 B1 | 9/2001 | Conley et al. | |
| 6,301,503 B1 | 10/2001 | Hsu et al. | |
| 6,415,175 B1 | 7/2002 | Conley et al. | |
| 6,418,340 B1 | 7/2002 | Conley et al. | |
| 6,449,504 B1 | 9/2002 | Conley et al. | |
| 6,535,763 B1 | 3/2003 | Hiebert et al. | |
| 6,718,198 B2 | 4/2004 | Conley et al. | |
| 6,721,594 B2 | 4/2004 | Conley et al. | |
| 6,843,801 B2 | 1/2005 | Conley et al. | |
| 6,941,167 B2 | 9/2005 | Stahmann et al. | |
| 7,418,295 B2 | 8/2008 | Conley et al. | |
| 2002/0151809 A1 | 10/2002 | Conley et al. | |
| 2005/0107840 A1 | 5/2005 | Conley et al. | |

OTHER PUBLICATIONS

"U.S. Appl. No. 09/372,157, Non-Final Office Action mailed Apr. 25, 2001", 9 pgs.

"U.S. Appl. No. 09/372,157, Request for Continued Examination mailed Dec. 7, 2001", 6 pgs.

"U.S. Appl. No. 09/378,406, Amendment and Response filed Jul. 27, 2001 to Non-Final Office Action mailed Apr. 27, 2001", 16 pgs.

"U.S. Appl. No. 09/378,406, Non-Final Office Action mailed Apr. 27, 2001", 6 pgs.

"U.S. Appl. No. 09/378,406, Notice of Allowance mailed Feb. 12, 2002", 5 pgs.

"U.S. Appl. No. 09/378,406, Notice of Allowance mailed Aug. 23, 2001", 6 pgs.

"U.S. Appl. No. 10/118,537, Amendment and Response filed Jul. 6, 2004 to Non-Final Office Action mailed Apr. 6, 2004", 10 pgs.

"U.S. Appl. No. 10/118,537, Notice of Allowance mailed Sep. 10, 2004", 5 pgs.

"U.S. Appl. No. 11/021,141, Response filed Oct. 26, 2007 to Office Action mailed Jul. 26, 2007", 9 pgs.

"U.S. Appl. No. 11/021,141, Non-Final Office Action mailed Jul. 26, 2007", 6 pgs.

"U.S. Appl. No. 11/021,141, Supplemental Notice of Allowability mailed Jun. 25, 2008", 3 pgs.

"U.S. Appl. No. 11/021,141, Notice of Allowance mailed Apr. 22, 2008", 4 pgs.

"Non-Final Office Action mailed Apr. 6, 2004", 4 pgs.

Conley, Vickie L., et al., "Arrhythmia Display", U.S. Appl. No. 10/747,391, filed Dec. 29, 2003, 24 pgs.

"U.S. Appl. No. 09/378,406, Non Final Office Action mailed Apr. 27, 2001", 6 pgs.

"International Application Serial No. PCT/US00/22644, International Preliminary Examination Report mailed Sep. 27, 2001", 6 pgs.

"International Serial No. PCT/US00/22644, International Search Report mailed Nov. 15, 2000", 3 pgs.

"International Application Serial No. PCT/US00/22644, Written Opinion mailed Jul. 25, 2001", 5 pgs.

* cited by examiner

METHOD AND SYSTEM FOR IDENTIFYING AND DISPLAYING GROUPS OF CARDIAC ARRHYTHMIC EPISODES

CROSS REFERENCE TO RELATED APPLICATION(S)

This application is a continuation of U.S. patent application Ser. No. 11/021,141, filed on Dec. 22, 2004, now issued as U.S. Pat. No. 7,418,295, which is a continuation of U.S. patent application Ser. No. 10/118,537, filed on Apr. 8, 2002, now issued as U.S. Pat. No. 6,843,801, which is continuation of U.S. patent application Ser. No. 09/378,406, filed on Aug. 20, 1999, now issued as U.S. Pat. No. 6,418,340, the specifications of which are incorporated herein by reference.

TECHNICAL FIELD

The present invention relates generally to medical devices and in particular to a system of analyzing cardiac data to identify and display groups of cardiac arrhythmic episodes.

BACKGROUND OF INVENTION

Implantable cardiac defibrillators (ICDs) are well established therapeutic devices for treating patients who have experienced one or more documented episodes of hemodynamically significant ventricular tachycardia or ventricular fibrillation. Since their clinical inception more than two decades ago, ICDs have evolved from basic to sophisticated electronic devices that provide physicians with a variety of clinically useful functions with which to treat patients.

Presently, even the most basic of ICDs typically has more than one tachycardia detection criterion, tiered therapy which combines bradycardia support pacing with various antitachycardia pacing modes, low-energy cardioversion, defibrillation, and data logging capabilities. The data logging capabilities within ICDs have become increasingly important, since the amount of data required for the ICDs operation increases proportionally with the increase in ICD functions. Efficiently processing this large amount of data has become possible with the incorporation of microprocessors and memory within the ICD.

Even with the advances in ICD data logging and processing capabilities, arrhythmia event recording capabilities have been limited, making it difficult to verify the adequacy and efficacy of arrhythmia detection and therapy settings. Furthermore, ICDs have been designed to record electrocardiogram and diagnostic channel data which can indicate to the physician the ICDs behavior during multiple tachyarrhythmic episodes. These ICDs also include arrhythmic event counters which log the number of episodes detected and the success or failure of each programmed therapy. Moreover, monitoring capability in some ICDs allow for recording of electrocardiogram waveforms, which can assist the physician in assessing the efficacy of the implanted ICD.

Once an ICD has been implanted, the physician interacts with the ICD through a clinical programmer. The clinical programmer is used to establish a telemetric link with the implanted ICD. The telemetric link allows for instructions to be sent to the electronic circuitry of the ICD and clinical data regarding the occurrence and treatment of a patient's cardiac arrhythmias and the ICD's operation to be sent from the electronic circuitry of the ICD to the clinical programmer. The typical programmer is a microprocessor-based unit that has a wand for creating the telemetric link between the implanted ICD and the programmer, and a graphics display screen that presents a patient's recorded cardiac data and ICD system information to the physician.

As the amount of cardiac data recorded by ICDs increases with each new generation of ICD, manufacturers and clinicians alike are becoming more sensitive to the role that time-efficient programming and data interpretation plays in the physician's clinical visit with the patient. As ICDs become increasingly complex, the interpretation of recorded arrhythmic episodes and the programming of the ICD can be challenging and time-consuming tasks for some users.

Therefore, a need exists for improved ICD and programmer technology that facilitates the identification of relevant information regarding the patient's clinical status. There is a need in the art for a system that facilitates the quick identification and presentation of groups of arrhythmic episodes within ICD recorded arrhythmic data.

SUMMARY OF THE INVENTION

The present disclosure describes a medical device system for analyzing cardiac data in order to identify and display groups of arrhythmic episodes. In one embodiment, the invention is directed toward a method of receiving the cardiac data representing a plurality of stored arrhythmic episodes, analyzing the cardiac data to identify a subset of stored arrhythmic episodes as a function of user-specified criteria, and displaying the subsets to an interactive screen of a medical device programmer.

According to the invention, only those episodes having characteristics that match the user-specified criteria are displayed. The criteria can be, but is not limited to, an arrhythmia type, a zone of detection, a date of occurrence and an average heart rate in beats per minute (BPM). By analyzing the cardiac data and only displaying the patient's recorded cardiac arrhythmic episodes of interest, the physician can more quickly assess and interpret the nature of the patient's cardiac arrhythmias and provide for more effective and efficient programming of the patient's ICD.

In another embodiment, the medical device system that comprises a cardiac defibrillator and a medical device programmer unit for the cardiac defibrillator. The cardiac defibrillator includes electronic control circuitry for determining and recording the occurrence of arrhythmic episodes of a heart. The programmer unit has programmer electronic circuitry that is coupled to an interactive display screen and which receives cardiac data representing a plurality of stored arrhythmic episodes from the electronic control circuitry. The programmer electronic circuitry analyzes the cardiac data to identify and displays a subset of stored arrhythmic episodes as a function of the user-specified criteria.

BRIEF DESCRIPTION OF THE DRAWINGS

In the drawings, where like numerals describe like components throughout the several views.

DETAILED DESCRIPTION

In the following detailed description, reference is made to the accompanying drawings which form a part hereof and in which is shown by way of illustration specific embodiments in which the invention may be practiced. These embodiments are described in sufficient detail to enable those skilled in the art to practice and use the invention, and it is to be understood that other embodiments may be utilized and that electrical, programmatic, and structural changes may be made without departing from the spirit and scope of the present invention. The following detailed description is, therefore, not to be taken in a limiting sense and the scope of the present invention is defined by the appended claims and their equivalents.

The embodiments of the present invention illustrated herein are described as being included in an implantable cardiac defibrillator, which may include numerous pacing modes known in the art, and an external medical device programmer. However, the medical system and method of the present invention could also be implemented in an external cardioverter/monitor system as are known in the art. Also, the medical system and method of the present invention could also be implemented in an implantable atrial cardioverter-defibrillator, which may include numerous pacing modes known in the art. Furthermore, although the present invention is described in conjunction with an implantable defibrillator having a microprocessor based architecture, it will be understood that the implantable cardiac defibrillator (or other implanted device) may be implemented in any logic based, custom integrated circuit architecture, if desired.

Figure 1:
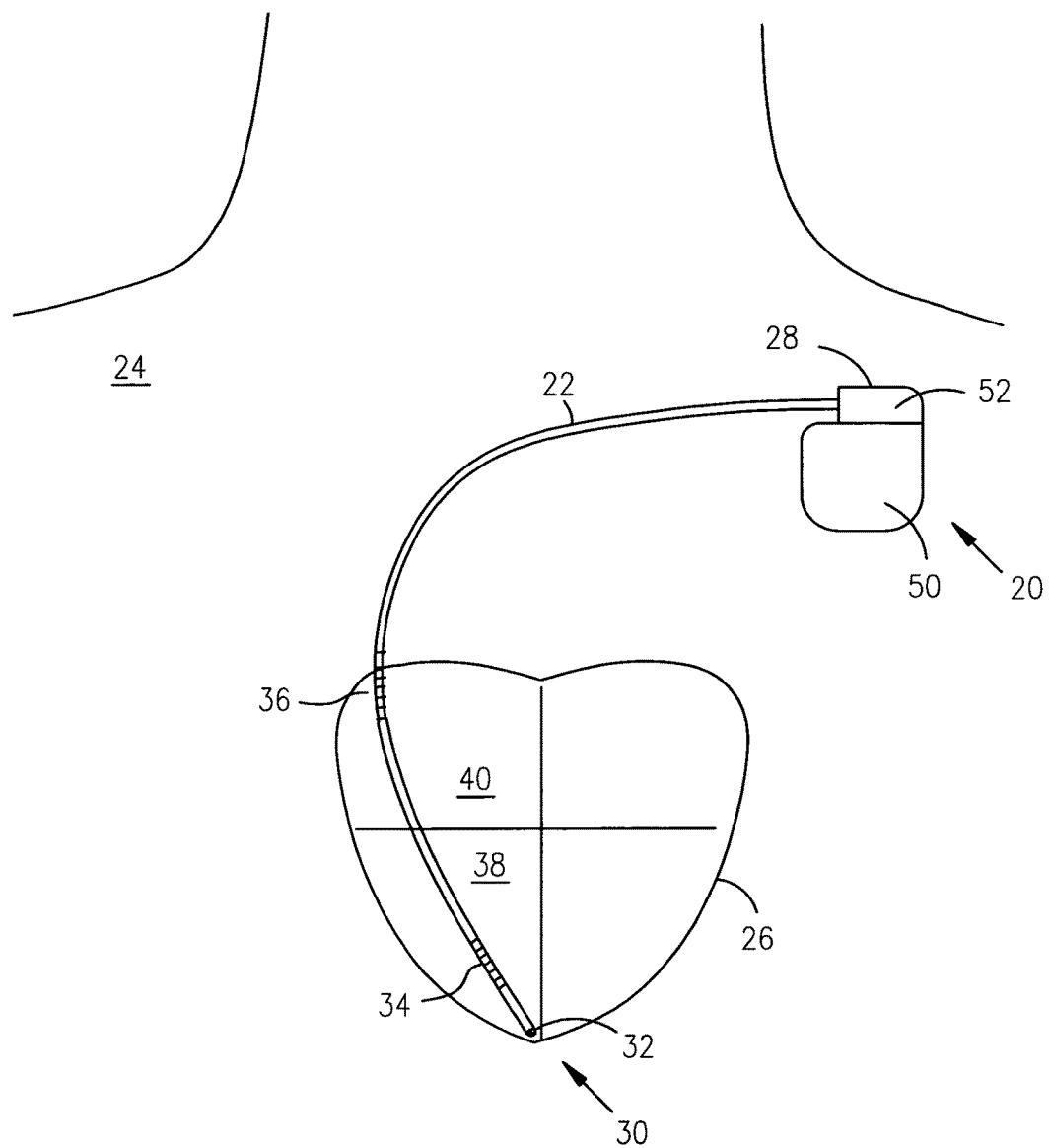
FIG. 1 is an embodiment of an implantable cardiac defibrillator implanted into a heart of a patient, from which portions have been removed to show detail.

Referring now to FIG. 1 of the drawings, there is shown one embodiment of a medical device system which includes an implantable cardiac defibrillator 20 electrically and physically coupled to at least one intracardiac catheter 22. In one embodiment, the intracardiac catheter 22 includes one or more pacing electrodes and one or more intracardiac defibrillation electrodes.

The intracardiac catheter 22 is implanted in a human body 24 with portions of the intracardiac catheter 22 inserted into a heart 26 to detect and analyze electric cardiac signals produced by the heart 26 and to provide electrical energy to the heart 26 under certain predetermined conditions to treat cardia arrhythmias, including ventricular fibrillation, of the heart 26.

In one embodiment, the intracardiac catheter 22 is an endocardial lead adapted to be releasably attached to the cardiac defibrillator 20. The intracardiac catheter 22 has an elongate body with a proximal end 28 and a distal end 30 and is shown as having a pacing electrode 32 located at, or adjacent, the distal end 30 of the intracardiac catheter 22. In one embodiment, the pacing electrode 32 is a tip electrode positioned at the distal end 30 of the intracardiac catheter 22. Alternatively, the pacing electrode 32 is an annular, or a semi-annular ring electrode positioned adjacent the distal end 30.

The intracardiac catheter 22 also includes one or more defibrillation electrodes. In one embodiment, the intracardiac catheter 22 has a first defibrillation electrode 34 and a second defibrillation electrode 36, where the first defibrillation electrode 34 and the second defibrillation electrode 36 are defibrillation coil electrodes as are known in the art. The first defibrillation electrode 34 is spaced apart and proximal from the pacing electrode 32, and the second defibrillation electrode 36 is spaced apart and proximal from the first defibrillation electrode 34 such that when the intracardiac catheter 22 is positioned within the heart 26 the pacing electrode 32 and the first defibrillation electrode 34 reside within a right ventricle 38 of the heart 26, with the pacing electrode 32 in an apex location within the right ventricle 38, and the second defibrillation electrode 36 is positioned within the right atrium chamber 40 of the heart 26 or a major vein leading to the right atrium chamber 40 of the heart 26.

Figure 2:
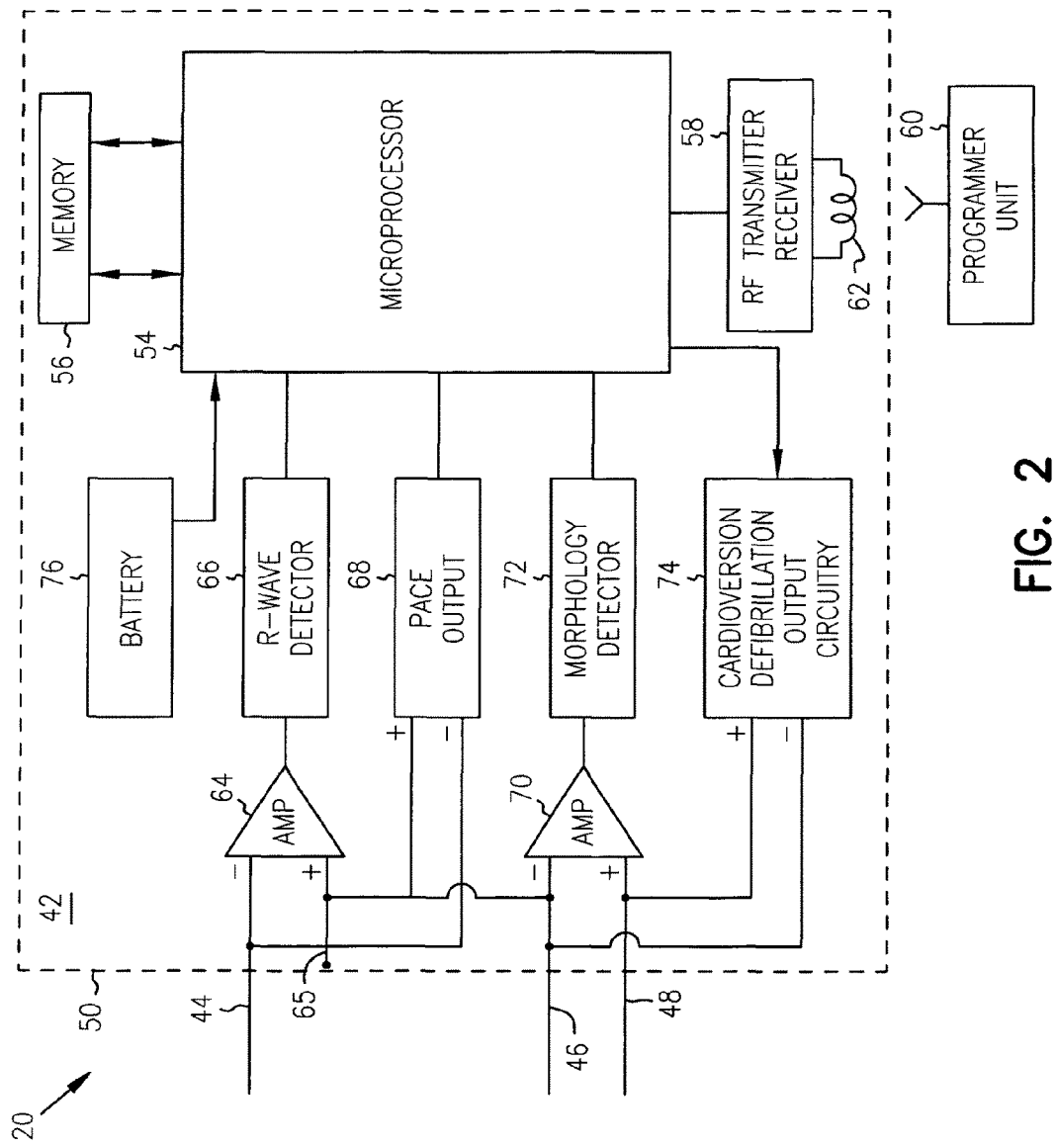
FIG. 2 is a block diagram of an implantable cardiac defibrillator according to one embodiment of the present invention.

Referring now to FIG. 2, there is shown an embodiment of a block diagram of a cardiac defibrillator 20. The cardiac defibrillator 20 includes electronic control circuitry 42 for receiving cardiac signals from a heart 26 and delivering electrical energy to the heart 26. The electronic control circuitry 42 includes terminals, labeled with reference numbers 44, 46, and 48 for connection to electrodes attached to the surface of the intracardiac catheter 22. The pacing electrode 32 is electrically connected to terminal 44 and to the electronic control circuitry 42 through an electrically insulated conductor provided within the elongate body of the intracardiac catheter 22. The first defibrillation electrode 34 and the second defibrillation electrode 36 are connected to terminals 46 and 48, respectively, and to the electronic control circuitry 42 through electrically insulated conductors provided within the elongate body of the intracardiac catheter 22.

In one embodiment, the electronic control circuitry 42 of the cardiac defibrillator 20 is encased and hermetically sealed in a housing 50 suitable for implanting in a human body. In one embodiment, titanium is used for the housing 50, however, other biocompatible housing materials as are known in the art may be used. A connector block 52 is additionally attached to the housing 50 of the cardiac defibrillator 20 to allow for the physical and the electrical attachment of the intracardiac catheter 22 and the electrodes to the cardiac defibrillator 20 and the encased electronic control circuitry 42.

The electronic control circuitry 42 of the cardiac defibrillator 20 is a programmable microprocessor-based system, with a microprocessor 54 and a memory circuit 56, which contains parameters for various pacing and sensing modes and stores data indicative of cardiac signals received by the electronic control circuitry 42.

A transmitter circuit 58 is additionally coupled to the electronic control circuitry 42 and the memory circuit 56 to allow the cardiac defibrillator 20 to communicate with a programmer unit 60. In one embodiment, the transmitter circuit 58 and the programmer unit 60 use a wire loop antenna 62 and a radio frequency telemetric link, as is known in the art, to receive and transmit signals and data to and from the programmer unit 60 and the electronic control circuitry 42. In this manner, programming commands or instructions are transferred to the microprocessor 54 of the cardiac defibrillator 20 after implant, and stored cardiac data pertaining to sensed arrhythmic episodes within the heart 26 and subsequent therapy, or therapies, applied to correct the sensed arrhythmic event are transferred to the programmer unit 60 from the cardiac defibrillator 20.

The embodiment of the cardiac defibrillator block diagram shows the pacing electrode 32 coupled to a sense amplifier 64. In an additional embodiment, the housing 50 of the cardiac defibrillator 20 is also coupled to the sense amplified 64 at 65 to allow for unipolar cardiac rate sensing between the pacing electrode 32 and the housing 50 of the cardiac defibrillator 20. The output of the sense amplifier 64 is shown connected to an R-wave detector 66. These components serve to sense and amplify the QRS waves of the heart, and apply signals indicative thereof to the microprocessor 54. Among other things, microprocessor 54 responds to the R-wave detector 66 by providing pacing signals to a pace output circuit 68, as needed according to the programmed pacing mode. Pace output circuit 68 provides output pacing signals to terminals 44 and 65, which connect to the pacing electrode 32 and the housing 50 of the cardiac defibrillator 20, for cardiac pacing.

The first defibrillation electrode 34 and the second defibrillation electrode 36 are coupled to a sense amplifier 70, whose output is connected to a cardiac morphology detector 72. These components serve to sense and amplify the QRS-waves of the cardiac cycle from the ventricular region of the heart 26, and apply signals indicative thereof to the microprocessor 54. In one embodiment, the cardiac morphology detector 72 includes an analog filter for filtering cardiac signal noise sensed by the electrodes. The cardiac signals are then band-limited before arriving at an analog-to-digital filter. The cardiac signals are then A/D converted into a digital signal and subsequently received by the microprocessor 54. In an alternative embodiment, the cardiac signals are filtered through an analog peak detector to extract the maximum and minimum cardiac signal values for each sensed cardiac interval.

The microprocessor 54 responds to the cardiac signals sensed within the heart 26 using the intracardiac catheter 22 by providing signals to cardioversion/defibrillation output circuitry 74 to provide either cardioversion or defibrillation electrical energy to the heart 26 depending upon nature of the arrhythmia sensed by the cardiac defibrillator 20. Power to the cardiac defibrillator 20 is supplied by an electrochemical battery 76 that is housed within the cardiac defibrillator 20.

For each arrhythmic episode sensed, cardiac defibrillator 20 stores episode data in memory circuit 56 as illustrated in Table 1. Other arrhythmic episode data known in the art can also be recorded and stored in the memory circuit 56.

TABLE 1

| STORED DATA | DESCRIPTION |
| --- | --- |
| Number | Episode number stored in chronological order. |
| Time stamp | Date and time of the episode. |
| Type | The type of episode detected such as spontaneous, induced, pacemaker-mediated tachycardia (PMT), atrial tachyarrhythmia response (ATR) or magnet activated. |
| Zone | The zone of detection which can be (VF), (VT), VT-1, Commanded, and Accelerated. |
| Rate | The average rate of the episode in beats per minute. |
| Therapy | Therapy that was delivered to the patient prior to detection including: none, one ATP, more than one ATP, one shock, more than one shock, ATP and shock. |
| Enhancement | Any detection enhancement criteria. |
| R-R Intervals | The time intervals between consecutively sensed R- waves for the episode. |
| EGMs | Data representing the sensed electrocardiogram signal such as a ventricular signal and an atrial signal. |
| Duration | The duration of the episode. |

Figure 3:
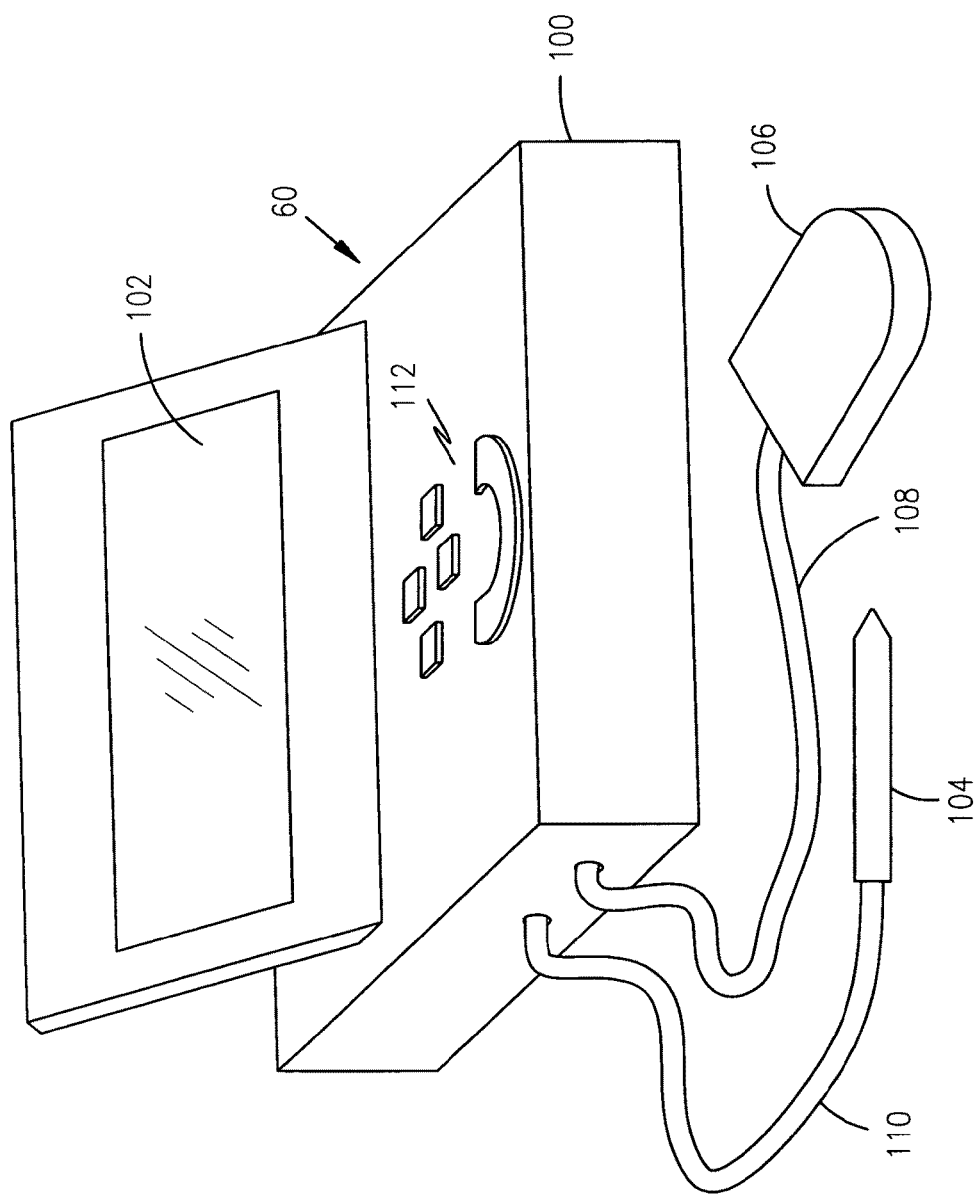
FIG. 3 is a perspective view of an external programming unit, according to one embodiment of the present invention, which is used for communicating with the implantable cardiac defibrillator of FIG. 1.

Referring now to FIG. 3, there is shown one embodiment of a medical device programmer 60 of the medical device system. As previously mentioned, one embodiment of programmer 60 for the implantable cardiac defibrillator 20 takes the form of an external controller as are known in the art. However, in an alternative embodiment, the medical device system is a completely external device such as an external cardioverting/defibrillator system as are known in the art, where the programmer unit is physically and electronically integrated into electronic control circuitry similar to the electronic control circuitry 42 of the cardiac defibrillator 20. An example of this latter embodiment is for an external cardiac monitor and defibrillation unit, electrically connected to the heart by any combination of intracardiac catheters, epicardial electrodes and/or externally cardiac electrodes, all of which are known in the art.

FIG. 3 shows one embodiment of programmer 60 designed to be positioned external of the human body 24 for communicating with an implantable medical device, such as the cardiac defibrillator 20 from FIG. 1, via RF telemetry. Programmer 60 has programmer electronic circuitry, including a microprocessing unit and related circuitry, such as digital memory, which is coupled to a graphics display screen 102.

In one embodiment, programmer 60 comprises an outer housing 100 which is made of a thermal plastic or other suitable lightweight durable material. The graphics display screen 102 is disposed on the upper surface of housing 100. The graphics display screen 102 folds down into a closed position when programmer 60 is not in use, thereby reducing the size of programmer 60 and protecting the display surface of graphics display screen 102 during transportation and storage.

In an additional embodiment, the external programmer additionally has a floppy disk drive and a hard drive disposed within the housing. Air vents are provided at various points in the housing 100 so that an internal fan can circulate air within the housing 100 and prevent overheating of components therein.

Programmer 60 is shown with the graphics display screen 102 positioned in one of a plurality of possible open positions such that a display on the graphics display screen 102 is visible to a user situated in front of programmer 60. In one embodiment, the graphics display screen 102 is of a liquid crystal display (LCD). The graphics display screen 102 is operatively coupled to the electronic circuitry disposed with the housing 100 and is adapted to provide a visual display of graphics and/or data under control of the programmer electronic circuitry.

Programmer 60 further includes a user input device coupled to the electronic circuitry. In one embodiment, the user input device is the graphics display screen 102, which is provided with touch-sensitive capability, such that a user can interact with the programmer electronic circuitry by touching the display area on the graphics display screen 102 with a stylus 104, or even the user's finger. In one embodiment, the touch-sensitive graphics display screen is primary input for programmer 60. Programmer 60 further includes a programming head 106, which is place over a patient's body near the implant site of an implanted device, such as the cardiac defibrillator 20, in order to establish a telemetry link between the cardiac defibrillator 20 and programmer 60. The telemetry link between the cardiac defibrillator 20 and programmer 60 allows the electronic circuitry coupled to the graphics display screen to be coupled to the electronic control circuitry of the cardiac defibrillator 20. The programming head 106 is coupled to the electronic circuitry of programmer 60 and a receiver circuit for receiving signals from the transmitter circuit indicative of cardiac signals by a cable 108.

The stylus 104 used to interact with the touch-sensitive graphics display screen 102 is coupled to the programmer electronic circuitry within the housing 100 by a cable 110. Alternatively, programmer 60 may be equipped with a conventional computer "mouse"-type pointing device, rather than a stylus. In the absence of either a stylus or a mouse, on-screen cursor control for enabling user interaction with programmer 60 may be facilitated through cursor control keys 112 (arrow keys or the like) disposed on programmer 60.

Programmer 60 further includes a receiver circuit for receiving signals from the transmitter circuit indicative of cardiac signals. Through the telemetric contact with the cardiac defibrillator 20, programmer 60 is capable of capturing and storing recorded electrocardiogram data transmitted from the cardiac defibrillator 20 and displaying the electrocardiogram data on its graphics display screen 102.

Figure 4:
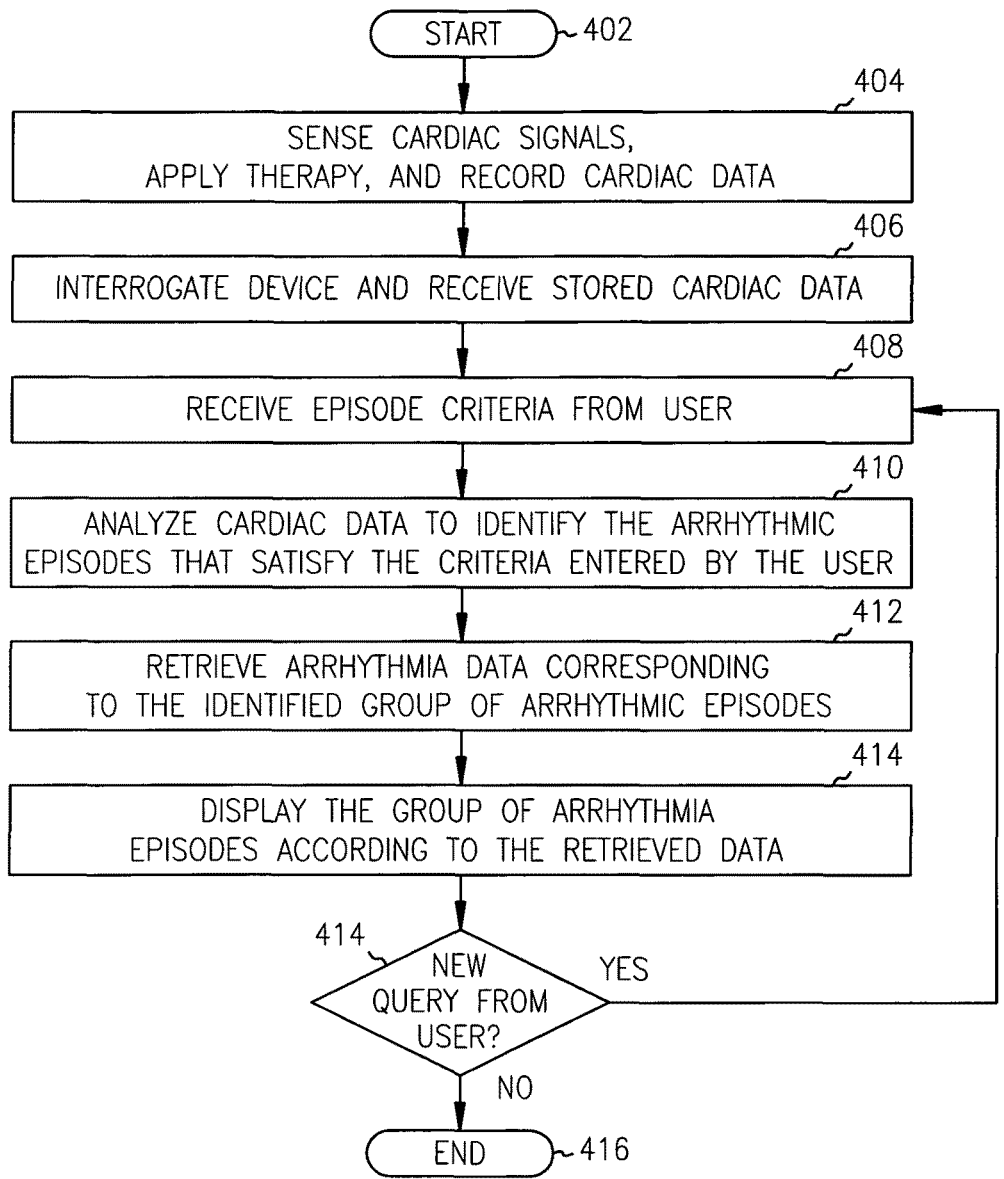
FIG. 4 is a flow diagram illustrating one mode of operation of an implantable cardiac defibrillator and a medical device programming unit incorporating the present invention.

FIG. 4 illustrates a flow diagram of one mode of operation of cardiac defibrillator 20 and programmer 60 according to the present invention. Process 400 begins at block 402 and proceeds to block 404 where cardiac defibrillator 20 senses signals representing arrhythmic episodes experienced by a patient and provides therapy for the sensed arrhythmic episodes. Cardiac defibrillator 20 electronically records cardiac data corresponding to the sensed arrhythmic episodes in memory 56. Such data includes an episode number, a type, etc. as described in Table 1 above. At block 406 programmer 60 interrogates the implanted cardiac defibrillator 20. During the interrogation, the stored data is transferred from the electronic control circuitry 42 and received by programmer 60.

After receiving the stored cardiac data from the cardiac defibrillator 20, programmer 60 displays a high-level summary of the recorded arrhythmic events in a spreadsheet-like format. This is typically a chronological textual list of a plurality of arrhythmic events recorded by the cardiac defibrillator 20. The summary of the recorded arrhythmic events displays the data described in Table 1 above such as a chronological number of the episode, the date and time of the episode, the type of episode detected, the onset rate of the episode, the stability of the episode, the duration of the episode, the average rate in beats per minute, and the type of therapy delivered.

In conventional systems, a user would need to manually scan through multiple episodes in order to identify and view relevant information. Programmer 60, however, provides a more convenient and more accessible way of identifying, viewing, and analyzing arrhythmic episodes of interest.

For example, in block 408 programmer 60 presents on display screen 102 one or more episode criteria inputs by which a user can input criteria in order to view a subset of the arrhythmic episodes received from cardiac defibrillator 20. In one embodiment programmer 60 presents six data filters that can be modified by the user as detailed in Table 2 below.

TABLE 2

| EPISODE CRITERIA | DESCRIPTION AND VALID PARAMETERS |
|---|---|
| Occurrence Date | Analyze data and identify episodes based on date of occurrence. Valid parameters include: all episodes, episodes that occurred since cardiac defibrillator 20 was last reset, and episodes falling with a specified range of dates. |
| Episode Type | Analyze data and identify episodes based on episode type. Valid parameters include: All, Spontaneous, Induced, PMT (pacemaker-mediated tachycardia), ATR (atrial tachyarrhythmia response) and Magnet (magnet induced). |

TABLE 2-continued

| EPISODE CRITERIA | DESCRIPTION AND VALID PARAMETERS |
|---|---|
| Zone | Analyze data and identify episodes the zone of detection which can be VF (ventricular fibrillation), VT (ventricular tachycardia), VT-1 (ventricular tachycardia), Commanded, Accelerated. |
| Therapy | Analyze data and identify episodes the therapy that was delivered to the patient prior to detection. Valid parameters include: none, one ATP (antitachycardia pacing), more than one ATP, one shock, more than one shock, ATP and shock. |
| Detection Range | Analyze data and identify episodes based on average beats per minute (BPM). Valid parameters include 90 to 250. |

In block 410 programmer 60 analyzes the cardiac data received from defibrillator 20 according to the criteria received from the user. In one embodiment, programmer 60 dynamically builds a query based on the entered criteria and queries an internal database, thereby identifying a set of stored episodes that satisfy the user's criteria. In one embodiment the database is maintained as a relational database. In another embodiment the database is maintained as one or more files on an internal hard disk or other removable media.

In block 412 programmer 60 retrieves the cardiac data that corresponds to the identified set of episodes. In block 414 programmer 60 processes the retrieved data and display the processed data on the interactive display screen 102. In one embodiment programmer 60 displays the set of episodes in a chronological spread-sheet style log. In another embodiment programmer 60 generates and displays a graphical depiction of the arrhythmic episodes. In a further embodiment, colors and/or the shapes of the symbols are used to further distinguish the selected arrhythmic events on the interactive display screen 102. The identified episodes may also be printed to a strip recorder or exported to a removable media.

Once the set of arrhythmic episodes is displayed, programmer 60 allows the user to enter new episode criteria. In block 414 programmer 60 determines whether the user wishes to enter a new query and repeats blocks 408, 410 and 414 if a new query is desired. If the user does not wish to enter a new query, process 400 proceeds to block 416 and terminates.

Figure 5:
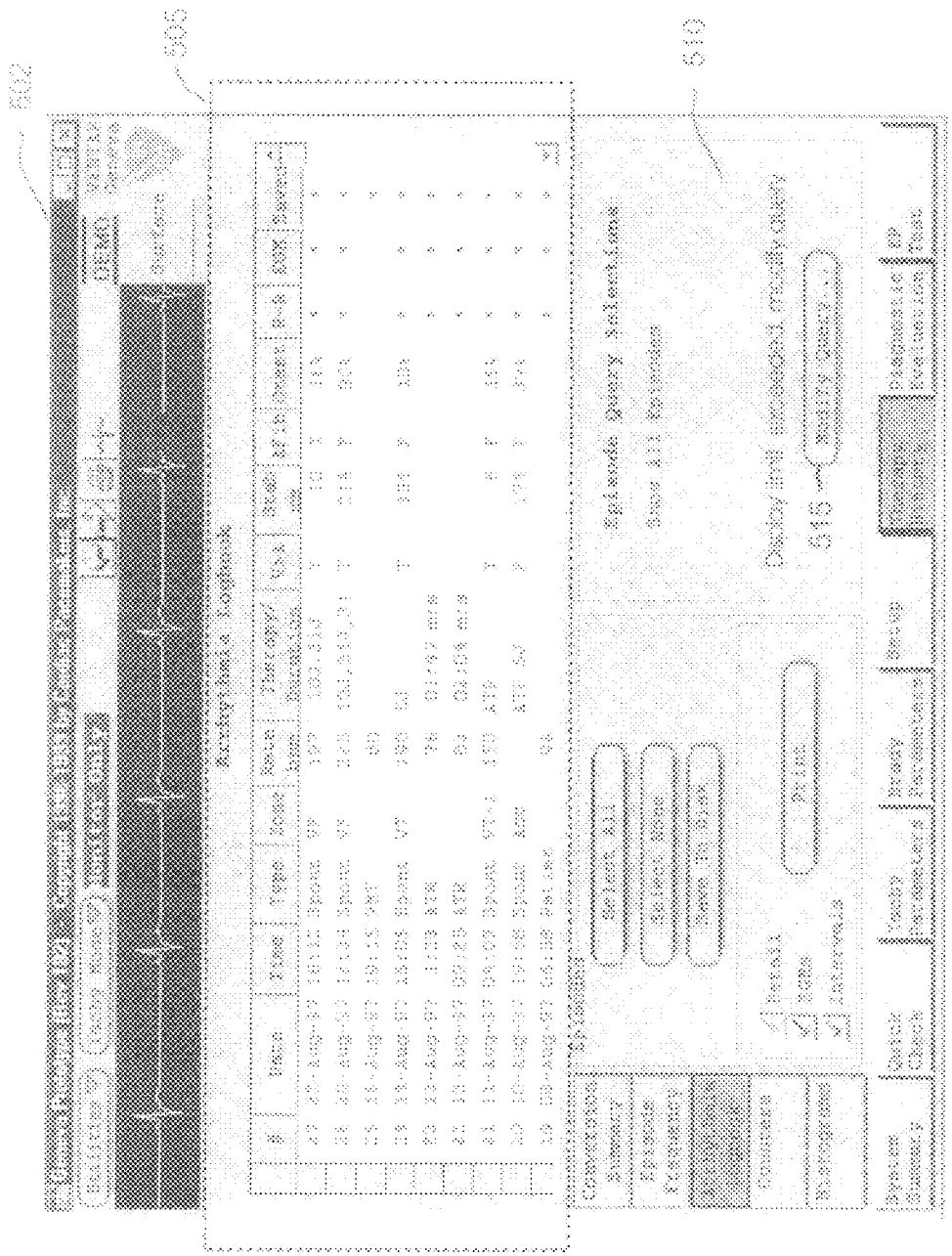
FIG. 5 illustrates a display screen presenting one embodiment of a summary window that, according to the invention, displays a set of arrhythmic episodes that are selected according to episode criteria specified by the user.

FIG. 5 illustrates display screen 102 presenting one embodiment of a summary window 502 that, according to the invention, identifies and displays a set of arrhythmic episodes according to episode criteria specified by the user. In the illustrated embodiment display screen includes a log window 505 that displays arrhythmic episodes in a spreadsheet format. More particularly, log window 505 has displays a plurality of arrhythmic episodes on tabular format, where each row corresponds to an individual episode. For each episode log window 505 displays various cardiac data as described in Table 1 above such as the episode number, a date and time that the episode was detected, a type of arrhythmia, zone of detection, beats per minute, therapy, duration, etc.

A query summary window 510 summarizes the selection criteria entered by the user in order to determine which arrhythmic episodes are displayed in log window 505. FIG. 5, therefore, illustrates that the user has elected to show all arrhythmic episodes received from cardiac defibrillator 20. If the user wishes to quickly and easily identify and view a subset of episodes, the user presses the modify query button 515 in order to modify the selection criteria.

Figure 6:
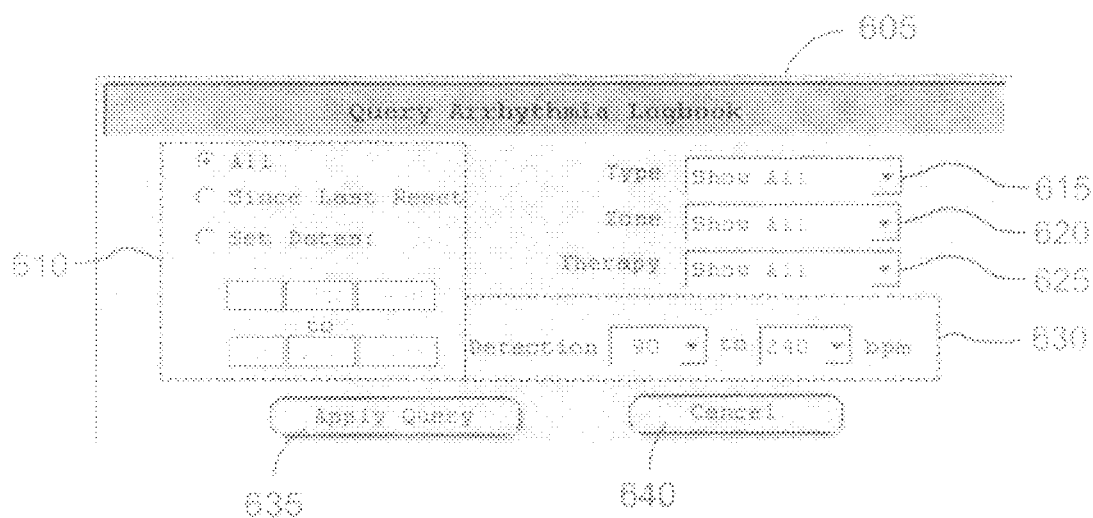
FIG. 6 illustrates the display screen presenting one embodiment of a query input window that contains a variety of pull down windows and other input fields by which a user enters criteria in order to identify and view a subset of the arrhythmic episodes received from cardiac defibrillator.

FIG. 6 illustrates display screen 102 presenting one embodiment of a query input window 605 that contains a variety of pull down windows and other input mechanisms by which a user enters criteria in order to view a subset of the arrhythmic episodes received from cardiac defibrillator 20. Using occurrence date input 610, the user instructs programmer 60 to analyze the data and identify those episodes based on a date of occurrence. More specifically, the user is able to select all episodes, only those episodes that occurred since cardiac defibrillator 20 was last reset, or episodes falling with a specified range of dates.

Via type selection 615, the user instructs programmer 60 to analyze data and identify episodes based on episode type. In one embodiment the user is able to select all types, spontaneous arrhythmias, induced arrhythmias, pacemaker-mediated tachycardia, atrial tachyarrhythmia response, and magnet induced arrhythmias. Similarly, using zone selection 620, a user instructs programmer 60 to analyze data and identify episodes based on the zone of detection which can be VF (ventricular fibrillation), VT (ventricular tachycardia), VT-1 (ventricular tachycardia), Commanded, Accelerated.

Rate selector 630 allows the user to analyze data and identify episodes based on an average beat per minute (BPM) for the duration of the episode. Valid parameters include 90 to 250 beats BPM. The user instructs programmer 60 via therapy selection 625 to analyze data and identify episodes according to the therapy that was delivered to the patient prior to detection. Here, valid parameters include: none, one ATP (antitachycardia pacing), more than one ATP, one shock, more than one shock, ATP and shock.

We claim:

1. A display screen of a medical device programmer for communicating with an implantable cardiac defibrillator, comprising:
a query summary window configured to summarize user-specified episode criteria; and
a log window configured to present a subset of arrhythmic episodes including episode data in a tabular format according to the user-specified episode criteria, the subset of arrhythmic episodes identified from cardiac data representative of a plurality of arrhythmic episodes using the user-specified episode criteria, the episode data indicating a number of antitachycardia pacing therapies and a number of shock therapies associated with each arrhythmic episode of the subset of arrhythmic episodes, the cardiac data received from the implantable cardiac defibrillator and including the episode data.

2. The display screen of claim 1, comprising a query input window configured to receive the user-specified episode criteria.

3. The display screen of claim 2, wherein the query input window comprises an occurrence date input field to receive a range of dates of occurrence.

4. The display screen of claim 2, wherein the query input window comprises a type selection input field to receive one or more episode types.

5. The display screen of claim 2, wherein the query input window comprises a zone selection input field to receive a zone of detection associated with detection criteria.

6. The display screen of claim 2, wherein the query input window comprises a rate selector input field to receive a detection range specified by average heart rates during each arrhythmic episode of the plurality of arrhythmic episodes.

7. The display screen of claim 2, wherein the query input window comprises a therapy selection input field to receive a parameter representing a therapy delivered prior to each arrhythmic episode of the plurality of arrhythmic episodes.

8. The display screen of claim 1, wherein the log window is configured to display the subset of arrhythmic episodes in a spreadsheet format.

9. The display screen of claim 8, wherein the log window is configured to display the subset of arrhythmic episodes in a tabular format in which each row corresponds an arrhythmia episode of the subset of arrhythmic episodes.

10. A method for operating a medical device programmer, comprising:
receiving cardiac data representative of a plurality of arrhythmic episodes from an implantable cardiac defibrillator;
displaying a query summary window on an interactive screen of the medical device programmer, the query summary window summarizing user-specified episode criteria;
identifying a subset of arrhythmia episodes from the cardiac data using the user-specified episode criteria; and
displaying a log window on the interactive screen, the log window presenting the subset of arrhythmic episodes including episode data of the cardiac data in a tabular format according to the user-specified episode criteria, the episode data indicating a number of antitachycardia pacing therapies and a number of shock therapies associated with each arrhythmic episode of the subset of arrhythmic episodes.

11. The method of claim 10, comprising displaying a query input window including a plurality of input fields to receive the user-specified episode criteria.

12. The method of claim 11, wherein displaying the query input window comprises displaying an occurrence date input field to receive a range of dates of occurrence.

13. The method of claim 11, wherein displaying the query input window comprises displaying a type selection input field to receive one or more episode types.

14. The method of claim 11, wherein displaying the query input window comprises displaying a zone selection input field to receive a zone of detection associated with detection criteria.

15. The method of claim 11, wherein displaying the query input window comprises displaying a detection range specified by average heart rates during each arrhythmic episode of the plurality of arrhythmic episodes.

16. The method of claim 11, wherein displaying the query input window comprises displaying a therapy selection input field to receive a parameter representing a therapy delivered prior to each arrhythmic episode of the plurality of arrhythmic episodes.

17. The method of claim 11, comprising receiving the cardiac data from an implantable medical device.

18. The method of claim 17, wherein displaying the log window comprises displaying the subset of arrhythmic episodes in a spreadsheet format.

19. The method of claim 18, wherein displaying the subset of arrhythmic episodes in the spreadsheet format comprises displayed the subset of the plurality of arrhythmic episodes in a tabular format in which each row corresponds an arrhythmia episode of the subset of arrhythmic episodes.

20. The method of claim 17, comprising displaying a graphical depiction of the subset of the plurality of arrhythmic episodes.

* * * * *